(12) United States Patent
Segal et al.

(10) Patent No.: US 7,769,549 B2
(45) Date of Patent: Aug. 3, 2010

(54) METHOD AND DEVICE FOR ON-LINE ACOUSTIC MONITORING OF FOAM AND AERATED FLUID PROPERTIES

(75) Inventors: Arkady Yurevich Segal, Moscow (RU); Marc Jean Thiercelin, Ville d'Avray (FR)

(73) Assignee: Schlumberger Technology Corporation, Cambridge, MA (US)

( * ) Notice: Subject to any disclaimer, the term of this patent is extended or adjusted under 35 U.S.C. 154(b) by 158 days.

(21) Appl. No.: 11/960,827

(22) Filed: Dec. 20, 2007

(65) Prior Publication Data

US 2009/0006005 A1 Jan. 1, 2009

(30) Foreign Application Priority Data

Dec. 28, 2006 (RU) .............................. 2006146964

(51) Int. Cl.
*G01N 31/00* (2006.01)

(52) U.S. Cl. .............................. 702/24; 702/35; 702/50; 702/100; 702/137; 702/189; 96/155; 96/176; 73/597; 52/309.4

(58) Field of Classification Search .................... 702/24, 702/35, 50, 100, 137–138, 155, 189; 52/309.4; 96/155, 176; 73/597
See application file for complete search history.

(56) References Cited

U.S. PATENT DOCUMENTS

| | | | | |
|---|---|---|---|---|
| 4,846,277 A | * | 7/1989 | Khalil et al. | 166/280.1 |
| 5,236,764 A | * | 8/1993 | Lenz et al. | 428/158 |
| 5,470,749 A | | 11/1995 | Djabbarah et al. | |
| 5,602,533 A | * | 2/1997 | Boverio | 340/686.5 |
| 5,741,978 A | | 4/1998 | Gudmundsson | |
| 6,461,414 B1 | | 10/2002 | Kohl et al. | |
| 2002/0116137 A1 | * | 8/2002 | Kirts et al. | 702/50 |

OTHER PUBLICATIONS

Nakajima et al., 'Measurement of Foam Quality of Activated Sludge in MBR Process', 2005, Ritsumeikan University Publication, pp. 232-239.*

Kieffer, S.W., Sound Speed in Liquid-Gas Mixtures: Water-Air and Water-Steam, Journal of Geophysical Research, vol. 82, No. 20, Jul. 10, 1977, pp. 2895-2904.

Tinge, J.T., et al., Ultrasonic gas analyser for high resolution determination of binary-gas composition, Journal of Physics E: Scientific Instruments, 19, 1986, pp. 953-956.

Gardiner, B.S., et al. Yield Stress measurements of aqueous foams in the dry limit, The Journal of Rheology, 42 (6), Nov./Dec. 1998, The Society of Rheology, Inc., pp. 1437-1450.

(Continued)

*Primary Examiner*—Eliseo Ramos Feliciano
*Assistant Examiner*—Elias Desta
(74) *Attorney, Agent, or Firm*—Brigid Laffey; James McAleenan; Vincent Loccisano

(57) ABSTRACT

A method for on-line acoustic detection of the quality of foams and aerated fluids whereby at least one emitter/receiver pair is placed in a close vicinity to the foam flow. At least one acoustic pulse is emitted and the time within which the acoustic pulse travels from the emitter to the receiver is recorded. Sound speed in the foam is determined by analyzing an acoustic response of the receiver and a pressure in the foam is also measured.

10 Claims, 10 Drawing Sheets

OTHER PUBLICATIONS

Falk, K., et al., Multiphase Pressure Pulses for Quick-Acting Valves: Offshore Testing, Society of Petroleum Engineers Annual Technical Conference and Exhibition, Houston, Texas, Oct. 1999, SPE 56526, pp. 1-11.

Herzhaft, B., Rheology of Aqueous Foams: a Literature Review of some Experimental Works, Oil & Gas Science and Technology—Rev. IFP, vol. 54, No. 5, 1999, pp. 587-596.

Gudmundsson, J.-S., et al., Two-Phase Flow Metering by Pressure Pulse Propagation, Society of Petroleum Engineers 67th Annual Technical Conference and Exhibition, Washington, D.C., Oct. 1992, SPE 24778, pp. 1-10.

Gudmundsson, J.S., et al., Gas-Liquid Metering Using Pressure-Pulse Technology, Society of Petroleum Engineers Annual Technical Conference and Exhibition, Houston, TX, Oct. 1999, SPE 56584, pp. 1-10.

Macias, L.C., Multiphase, Multicomponent Compressibility in Petroleum Reservoir Engineering, Society of Petroleum Engineers 61st Annual Technical Conference and Exhibition, New Orleans, LA, Oct. 1986, SPE 15538, pp. 1-8.

Sporker, H.F., et al., System Design for the Measurement of Downhole Dynamic Rheology for Foam Fracturing Fluids, Society of Petroleum Engineers 66th Annual Technical Conference and Exhibition, Dallas, TX, Oct. 1991, SPE 22840, pp. 1-9.

Valko, P., et al., The Rheological Properties of Carbon Dioxide and Nitrogen Foams, Society of Petroleum Engineers International Symposium on Formation Damage Control, Lafayette, LA. Feb. 1992, SPE 23778, pp. 1-12.

Wood, A.B., et al., A Textbook of Sound, G. Bell and Sons Ltd., London, 1964, pp. 245-272.

\* cited by examiner

SURFACE QUALITY=0.01

FIG.5 SURFACE QUALITY=0.1

METHOD AND DEVICE FOR ON-LINE ACOUSTIC MONITORING OF FOAM AND AERATED FLUID PROPERTIES

FIELD OF THE INVENTION

This invention relates to the method and device for on-line acoustic monitoring of properties of foams and aerated multiphase fluids with a complex rheology. This invention can be applied for on-line detection of the quality of foams and aerated fluids, i.e. the assessment of the gas fraction in gas-containing fluids, in particular, in the oil production sector during well maintenance activities, including well cementing or formation fracturing operations. This invention can be implemented in any field of the industry, e.g., in the food industry to produce carbonated beverages as well as in the pharmaceuticals industry.

BACKGROUND OF THE INVENTION

Definition: a ratio of a volume of gas contained in a fluid to the total volume of fluid and gas is called as the "quality" and is designated as "Γ".

$$\Gamma = \frac{V_1}{V}, \quad (1)$$

where: $V_1$—gas volume, V—total fluid & gas volume.

As follows from the definition, Γ falls within a range of 0 to 1. If Γ<0.5, the fluid is called as the "aerated fluid"; If Γ>0.5, the fluid is called as the "foam". In this context, the "foam" term will be applied to the both cases. e.g., the foam quality of 0.9 means that the foam consists of 90% of gas and 10% of fluid.

Well cementing operations are required to provide a long-term stability of wells subjected to the formation pressure impact. Cementing is performed by injecting a cement slurry in a well through a pipe string; after that, the cement slurry is allowed to harden. In some cases, it's expedient to add some gas in the injected slurry to foam it up and to produce a lighter cement slurry; in so doing, it's important to correctly determine the quality "Γ" of the foamed cement slurry which is injected into the well. A proper determination of the foamed cement slurry quality is a major integral component of well-cementing activities, since this factor defines mechanical properties of cements and, therefore, the stability of well operation.

A formation fracturing process aims to enhance well productivity by forming or enlarging channels connecting the wellbore with the oil-bearing formation. This operation is achieved through the injection of a fracturing fluid into a well that passes through the underground rock beds, and the pressurized fracturing fluid injection into the underground rock beds. In this process, hard rocks start fracturing and one or several fractures either form, or enlarge. A fracturing fluid contains a propping agent (proppant) that occupies the fracture volume and prevent the fracture from closing. Therefore, an increased flow rate of oil, gas and water is provided. In some cases, foams or aerated fluids are applied as a fracturing fluid either to reduce a wellhead pressure, or to improve the removal of well fluids from the fractured area.

In the industry, the foam quality is generally determined by a direct measurement of the gas and fluid volumes in the foam; for this purpose, different methods and different tools are used. For example, this can be implemented by creating a special discharge contour en-route the foam flow direction, which comprises a chamber for gas separation from the foam, and a direct measurement of the gas volume, or a flowmeter-based measurement of a flow for each phase.

The U.S. Pat. No. 6,461,414 discloses a system for determination and control (if required) over the foam-forming process for a fluid that comes from the underground formation and passes through at least one gas-to-fluid separator where gas is removed from the formation fluid entering there from the underground formation. The system comprises a transducer for measuring a required parameter of a gas flow isolated from the formation fluid, which is a foam-forming indicator for the formation fluid. The system also includes a processor for processing of measured parameters as well as for the determination of the foam-formation ratio for the formation fluid.

The system additionally comprises a gas separator, i.e. a device for gas fraction separation from the gas stream to form a side-cut fraction; the said transducer measures the side-cut fraction parameters. A hollow shaft can be applied as the said separator. Either a densitometer, the device for measuring the density or optical density of a fluid in the gas stream, or a gas stream optical density transducer can be employed as the above-mentioned transducer.

To determine the foam-formation ratio, a gas sample is taken from the high pressure separator, and then either the sample density, or the oil flow rate are measured. After that, the relationship between the density or optical density and foam-formation ratio is established; the received signal is transmitted to a control device. The supply of at least one foam-foaming additive is controlled to effect control over the foam-forming process. Part of the flow should be sent to a bypass pipeline for forming a side flow to determine the foam quality in the flow; this deems to be a disadvantage of the system described above. The system does not allow the determination of the foam quality directly in the pipeline a fluid from the underground formation passes through. The application of a separator while defining the foam quality is a reason of high error occurrence.

The U.S. Pat. No. 5,470,749 discloses a method for continued measurement of a steam flow, which is employed for pressurized well injecting (with the aim to enhance oil production) at pressures which are much higher than the atmospheric pressure, and at a room temperature. This method calls for the following:

a) vapor of a known-quality (vapor volume to vapor & fluid volume ratio) is mixed with a surfactant—max 1% of vapor's fluid phase weight to form a stable foam with a quality which is on par with the vapor quality, b) stable foam is directed through a non-conductive shielded capillary tube and a voltage drop between two electrodes located across the given tube length as well as a pressure drop across the same given tube length are measured, c) the above-mention steps are repeated, using different quality vapors, d) voltage drop vs. pressure drop diagram is plotted to define the foam quality (vapor volume to vapor & fluid volume ratio) for each vapor sample, e) a sequence of vapor flow samples of unknown quality is removed and the steps a), b) are repeated for each sample to determine a ratio between the pressure drop and the pressure of a stable foam formed from the said vapor; thereafter, a temperature of the stable foam formed from the said vapor is measured to define the fluid-water and water-vapor phase volumes for the stable foam-forming flow, f) quality of each sample of the stable foam is graphically determined at the step e) based on the relationship between the foam quality and voltage drop vs. pressure drop ratio, drawn at the step d), which is equal to the vapor quality, g) vapor quality (vapor volume to foam volume ratio) obtained at the step f) for each sample is converted to the vapor quality (vapor weight per vapor & fluid weight), using a specific volume of the fluid-water and water-vapor phases determined at the step e).

The disadvantage of this method is that, when it's required to define the foam quality, first it is necessary to converse vapor into a stable foam and then to take off part of the flow to the bypass pipeline, from which samples are then taken.

In case of the foam flow branching, e.g., during the formation hydraulic fracturing or well cementing activities, this method does not allow direct determination of the foam quality distribution. In this case, the quality is calculated theoretically or by using numerical simulations; for this purpose, quality data at accessible points of the flow (e.g., at the slurry injection point) or the injection diagram (or both) are specified. These measurements are impossible in industrial conditions, when monitoring of remote inaccessible sections (through which foam supply is arranged) is required.

It's possible to measure foam quality indirectly (i.e., not by measuring foam-forming gas & fluid volumes), using the monitoring of the foam physical properties.

As the nearest engineering approach, a method for the foam quality determination through a monitoring of the foam physical characteristics, which are dependent of the foam quality, can be considered. A speed of sound in the foam is one of the above-mentioned characteristics. The indicated sound speed vs. foam quality relationship is disclosed, e.g., in A. B. Wood's publication <<Textbook of Sound>>(London, 1964). The simplest example is a two-phase foam comprising a perfect gas and a non-viscous fluid. For this foam, sound speed is connected with the foam quality as follows:

$$C_{fm}^2 = N \frac{p}{\rho_{fl}(1-\Gamma)\Gamma} \quad (2)$$

where: $C_{fm}$—speed of sound in foam, p—pressure, $\rho_{fl}$—fluid density, $\Gamma$—foam quality, N—polytrophic expansion coefficient (reference value, e.g., N=1 for isothermal process, N=1.4 for adiabatic process).

FIG. 1 shows the water foam sound speed relationship at p=10 MPa. It's also should be mentioned that a typical sound speed $C_{fm}$ in foams is many-fold lower than the sound speed $C_{lq}$ in the reference fluid. This relationship is well-ascertained experimentally (e.g., ref. to K. Falk, J-S. Gudmundsson's publication <<Multiphase Pressure Pulses for Quick -Acting Valves: Offshore Testing>>, SPE 56526, or B. S. Gardiner <<Yield Stress measurements of aqueous foams in the dry limit >>, The journal of Rheology, 42(6), November/December, 1998). In S.W. Kieffer <<Sound Speed in Liquid-Gas mixtures: Water-Air and Water Steam >>(Journal of Geophysical Research, Volume 82, B20, 1977, pages 2895-2904), there is an example of the state-of-the-art theoretical analysis, which also confirms the applicability of Formula (1) for the foam quality determination.

For multi-phase multi-component fluid & gas mixtures, the sound speed vs. phase volume ratio relationship could either be measured in laboratory conditions (e.g., ref. to B. S. Gardiner's publication <<Yield Stress measurements of aqueous foams in the dry Limit>>), or calculated theoretically (e.g., ref. to B. Herzhaft's publication <<Rheology of Aqueous Foams: a Literature Review of some Experimental Works, >>Oil & Gas Science and Technology Rev. IFP, Vol. 54(1999), No. 5, pp. 587-596), which discloses a method for determining a mixture compressibility factor which predetermines the speed of sound in media.

Therefore, the foam quality can be defined by measuring a pressure and sound speed in the foam; a particular profile of the curve characterizing the relationship between the foam quality and pressure & sound speed can be found either analytically, or experimentally, or by numerical simulations. This relationship is hereinafter referred to as the <<chart>>.

Due to a strict sound speed vs. foam quality relationship, there is an opportunity of detecting the foam quality based on the results of integrated measurements of the sound speed and pressure in the foam. This opportunity becomes more attractive, in particular, owning to the emergence of innovative technologies for on-line well pressure measurement, e.g., by using optical fibers.

The sound speed vs. foam quality relationship is used in metering tools. A device for measuring the sound speed in binary gas mixtures to determine concentration variation for one component of the said mixture is known (e.g., ref. to Tinge J. T, et. al., <<Ultrasonic gas analyzer for high resolution determination of binary-gas composition,>>Journal of Physics E: Scientific Instruments, 19, 1986, pp. 953-956)).

A method of multi-phase fluid flow measurement for offshore wells is known (e.g., ref. to U.S. Pat. No. 5,741,978, Method for Determination of Flow Rate In a Fluid, J. S. Gudmundsson or to the publications of J. S. Gudmundsson et. al. <<Gas-Liquid Metering Using Pressure -Pulse Technology >>, SPE 56584and <<Two-Phase Flow Metering by Pressure Pulse Propagation>>, SPE 24778). All the above-mentioned methods are based on the specified sound speed vs. foam quality relationship.

However, known methods and devices do not allow to determine the quality of a foam, which is used in, e.g., well cementing or hydraulic fracturing of formations or in other industries, in the real time mode by conducting acoustic measurements.

SUMMARY OF THE INVENTION

From the engineering point of view, this invention aims to develop a method and device for foam quality monitoring, which would allow the on-line measurement of the speed of the sound and foam pressure, which are then applied to define foam quality in the real-time mode.

The task we assigned for ourselves was resolved by the development of an on-line foam quality acoustic monitoring, which calls for the following steps:

at least one emitter/receiver pair is placed in close vicinity to foam flow, at least one acoustic pulse is emitted, time, within which the acoustic pulse overcomes the way from the emitter to the receiver, is recorded, acoustic pulse speed (sound speed) is determined by analyzing an acoustic response of the receiver, pressure in the foam in the area between the emitter and receiver is defined, foam quality $\Gamma$ is calculated using the equation:

$$\Gamma = \frac{1}{2} \pm \sqrt{\frac{1}{4} - \frac{N}{\rho_{fl}} \frac{p}{C_{fm}^2}}, \quad (3)$$

where: $C_{fm}$—, speed of sound in the foam, p—pressure, $\rho_{fl}$—fluid density, $\Gamma$—foam quality, N—polytrophic expansion coefficient (reference value, N=1 for isothermal process; N=1.4 for adiabatic process) in case of a foam composed of a perfect gas and a perfect fluid, or in more complicated cases, it can be found from a chart.

It's worth mentioning that there are two values of the quality, which are associated with the same foam sound speed & pressure values; this fact corresponds to the <<±>> sign in the formula, meanwhile the sum of these two values is equal to 1. That's why for cases, in which the foam quality is supposedly much lower than ½ or much bigger than ½, the sign to be selected in the said formula is <<−>> and<<+>>, respectively. This fact brings a minor uncertainty to the applied method, since the required operations give us a well-known approximate gas fraction in the fluid and it's clear that $$\Gamma \leq \frac{1}{2} \text{ or } \Gamma \geq \frac{1}{2}$$

and, therefore, it's clear which sign shall be taken in the formula. In cases when both values of $\Gamma$ are near ½ the both quality values should be considered as a possible option.

It's expedient to place at least one the above-mentioned emitter/receiver pair along the foam flow direction and to measure sound speed at several points downstream of the foam flow to obtain the foam quality vs. flow direction profile. Preferably to install an emitter/receiver pair at the wellhead to emit sound at the foam flow beginning and to receive a signal reflected from the foam flow end. For the purpose of monitoring over the continued foam quality distribution, it's useful to continuously measure pressure along the foam flow direction.

The established task was also resolved by developing a device for on-line foam quality acoustic monitoring, comprising at least one emitter/receiver pair located in close vicinity of the foam flow and intended to emit at least one acoustic pulse and to receive at least one acoustic response, a logger to record the time required for the acoustic pulse to travel from the emitter to the receiver, pressure transducer placed between the emitter and the receiver, data processing unit connected to at least one emitter/receiver, the logger and pressure transducer, which is intended to calculate the sound speed using the acoustic pulse travel time, and to calculate the foam quality $\Gamma$ based on data received from the equation $$\Gamma = \frac{1}{2} \pm \sqrt{\frac{1}{4} - \frac{N}{\rho_{fl}} \frac{p}{C_{fm}^2}}, \quad (3)$$

where: $C_{fm}$—speed of sound in the foam, p—pressure, $\rho_{fl}$—fluid density, $\Gamma$—foam quality, N—polytrophic expansion coefficient (reference value, N=1 for isothermal process; N=1.4 for adiabatic process), in case of a foam composed of a perfect gas and a perfect fluid for cases, when the foam quality is supposedly much lower than ½ or much bigger than ½, the sign to be selected in the said formula is <<−>> and <<+>> respectively; in cases when both values of $\Gamma$ are near ½, the both quality values should be considered as a possible option, or in more complicated cases, it can be found from a chart, a comparison unit to compare values defining foam quality, with the chart for more complicated cases.

It's expedient to place at least one the above-mentioned emitter/receiver pair could be moved along the foam flow direction to measure sound speed at several points downstream of the foam flow to obtain the foam quality vs. flow direction profile. It's useful to install at least one emitter/receiver pair in the close vicinity of the wellhead to emit sound at the foam flow beginning and to receive a signal reflected from the foam flow end.

BRIEF DESCRIPTION OF THE DRAWINGS

Further on, the invention is explained by a description of its preferred embodiments, with references to associated drawings showing the following.

DETAILED DESCRIPTION OF THE PREFERRED EMBODIMENTS

Figure 2:
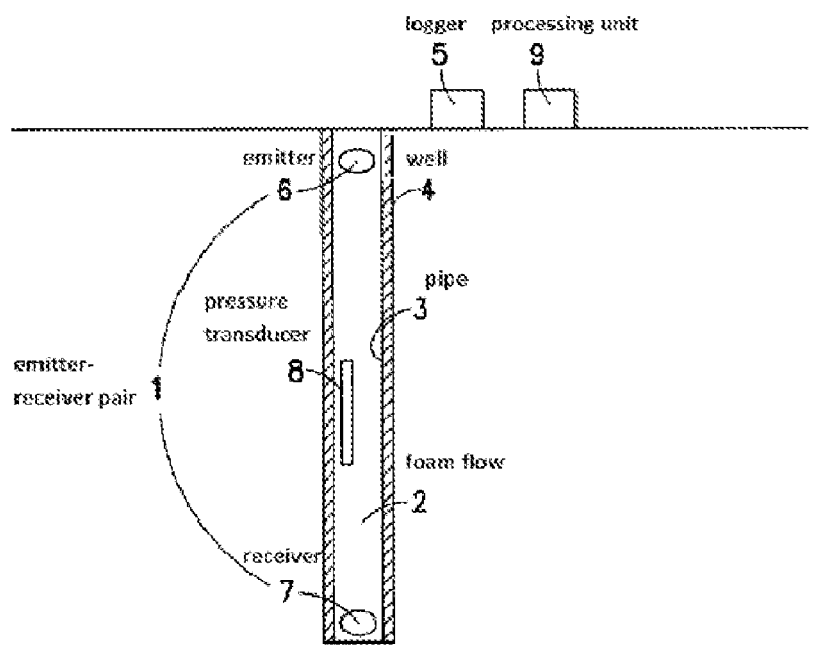
FIG. 2 shows an on-line foam quality acoustic monitoring system as per the invention.

A device for on-line foam quality acoustic monitoring is shown in FIG. 2 and includes at least one emitter-receiver pair (1) located in the close vicinity of the foam flow (2) and intended to emit at least one acoustic pulse and to receive the acoustic response. The foam flow passes through a pipe (3) in the well (4). The device also includes the logger (5) to record the time required for acoustic pulse to travel from the emitter (6) to the receiver (7). The pressure transducer (8) is mounted between the emitter (6) and the receiver (7).

The device also includes the data processing unit (9) connected with at least one emitter (6)/ receiver (7), logger (5) and pressure transducer (8) and is designed to calculate speed of sound based on the acoustic pulse arrival time and to calculate the foam quality $\Gamma$ based on data received as per equation (3) in case of a foam composed of a perfect gas and a perfect fluid, or in more complicated cases, it can be found from the chart. Another option is possible. In this embodiment, at least one the above-mentioned emitter/receiver pair (1) can move along the foam flow direction to allow sound speed measurement at several points along the foam flow direction to obtain foam quality distribution along the flow path.

Figure 3:
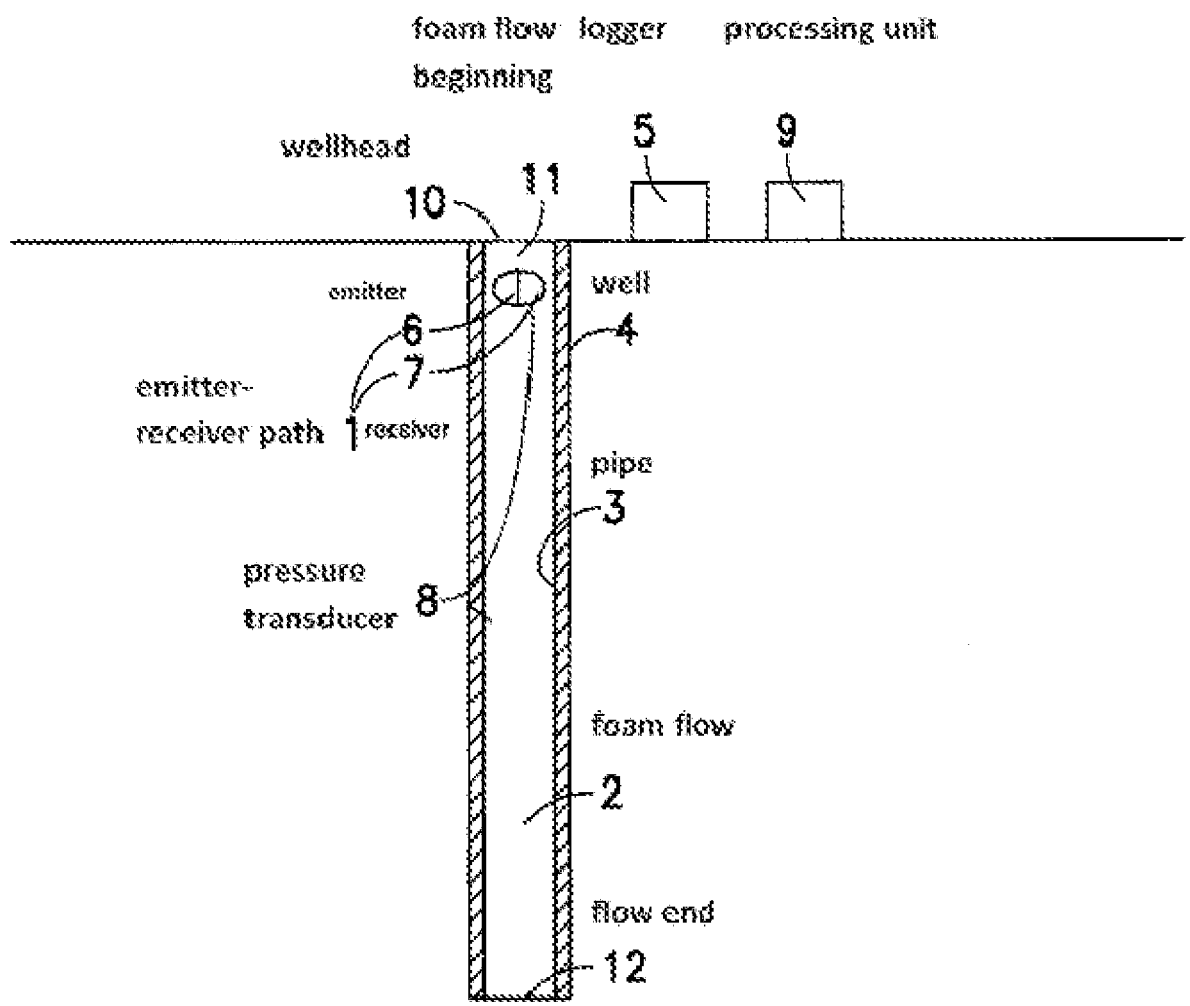
FIG. 3 shows a second embodiment for the on-line foam quality acoustic monitoring system as per the invention.
Figure 4:
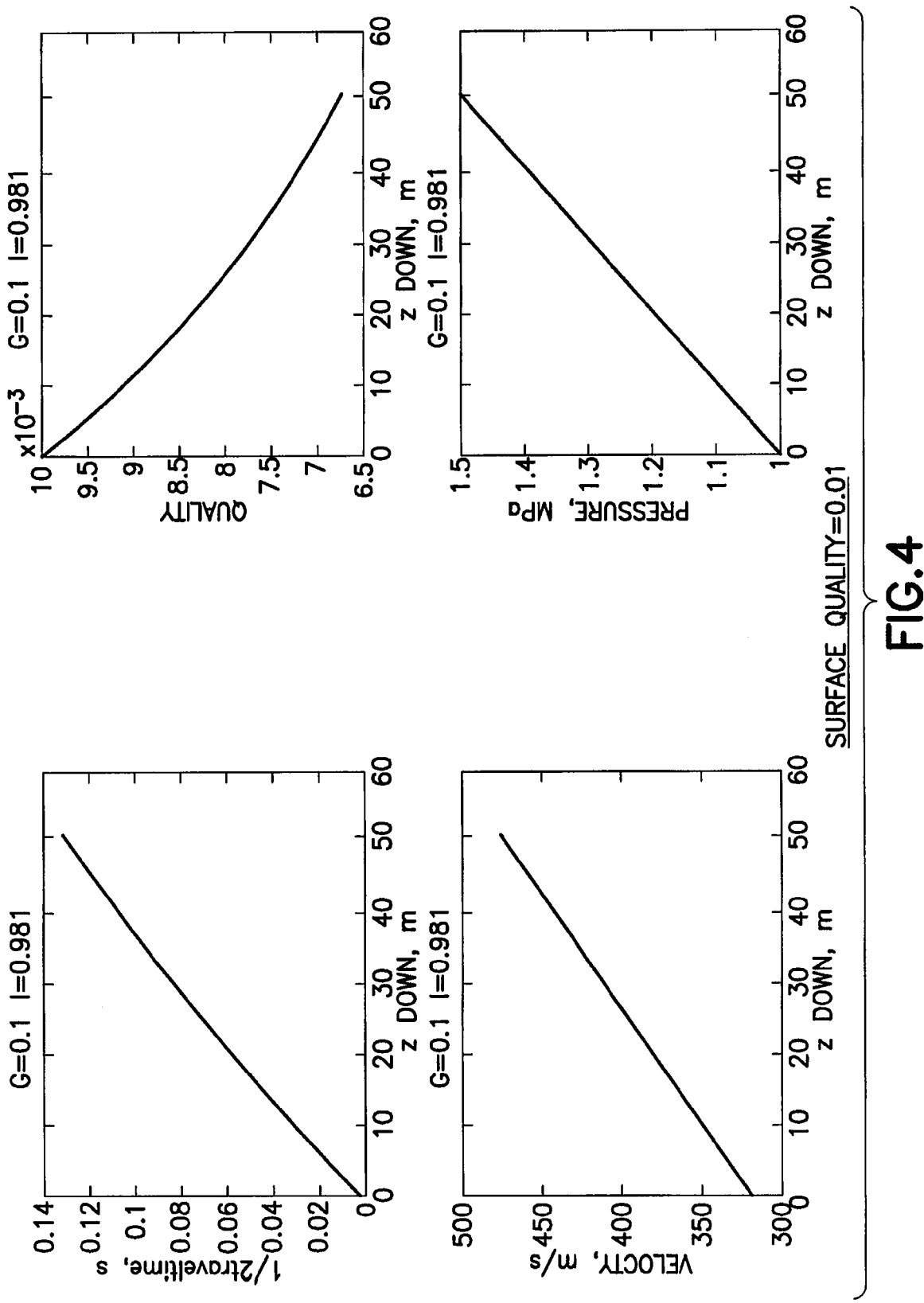
FIGS. 4-10 show distribution diagrams for quality and pressure & sound speed parameters as well as time of sound travel from the surface to the point "z" at various surface conditions, as per the invention.
Figure 5:
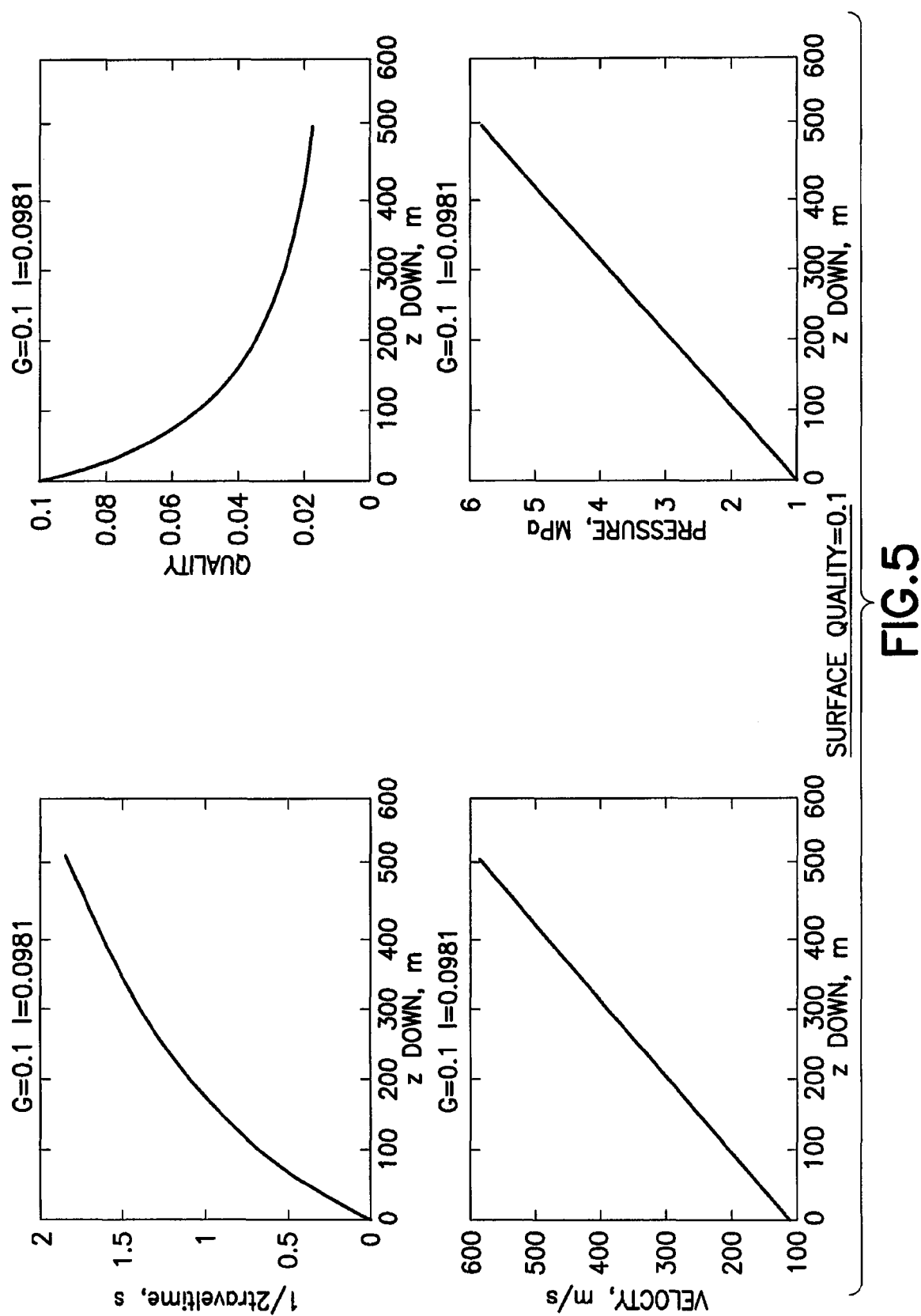
Figure 6:
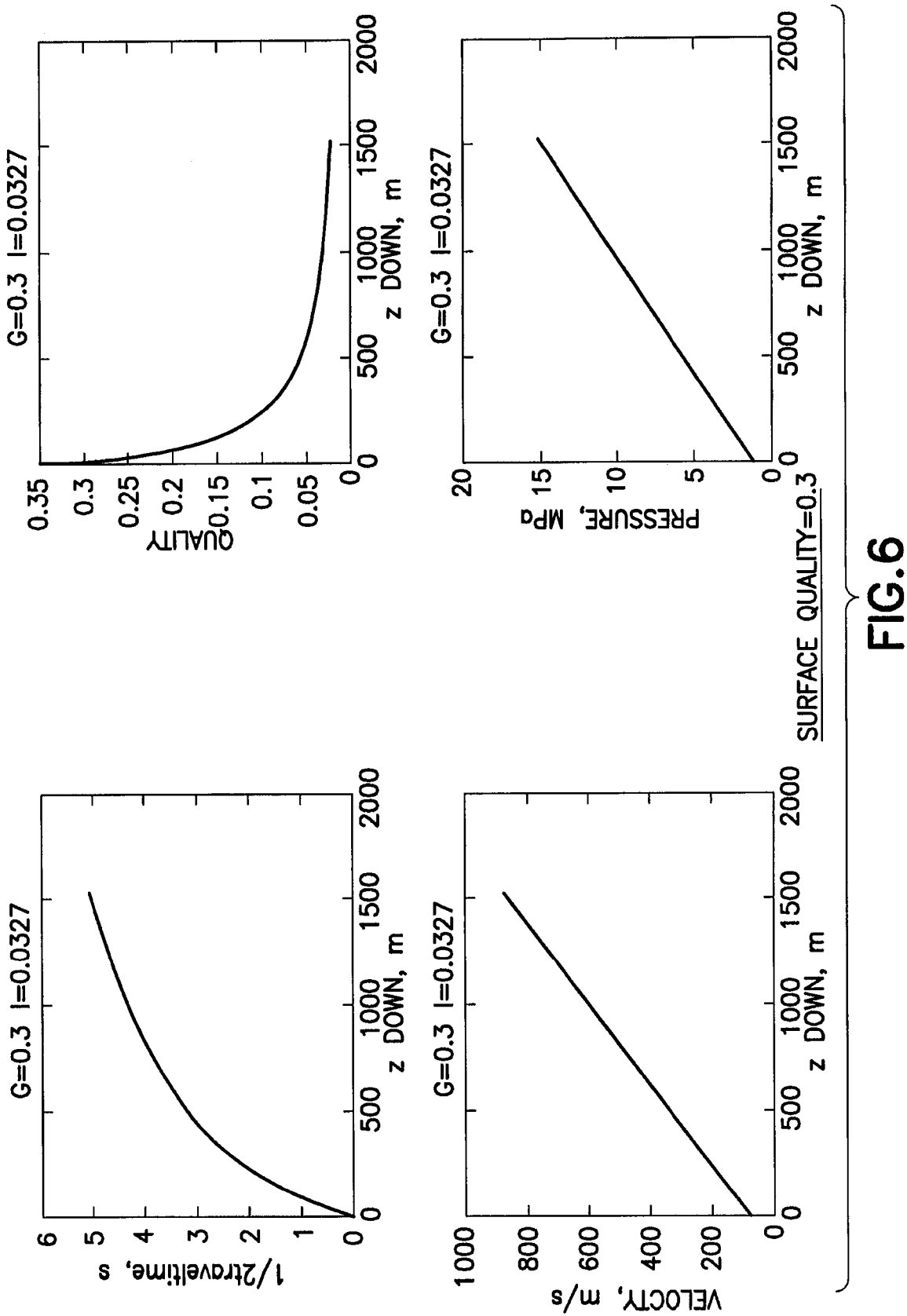
Figure 7:
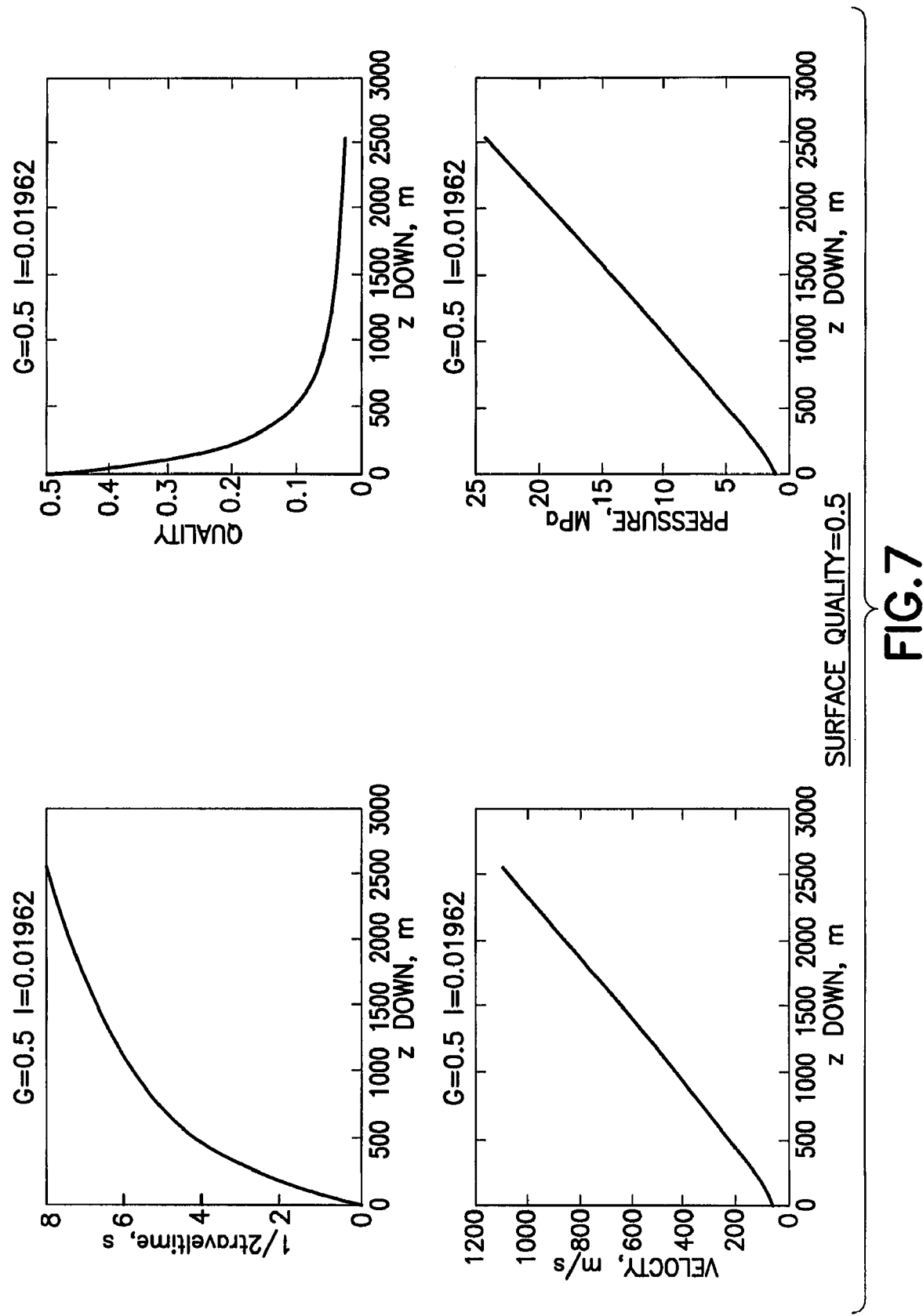
Figure 8:
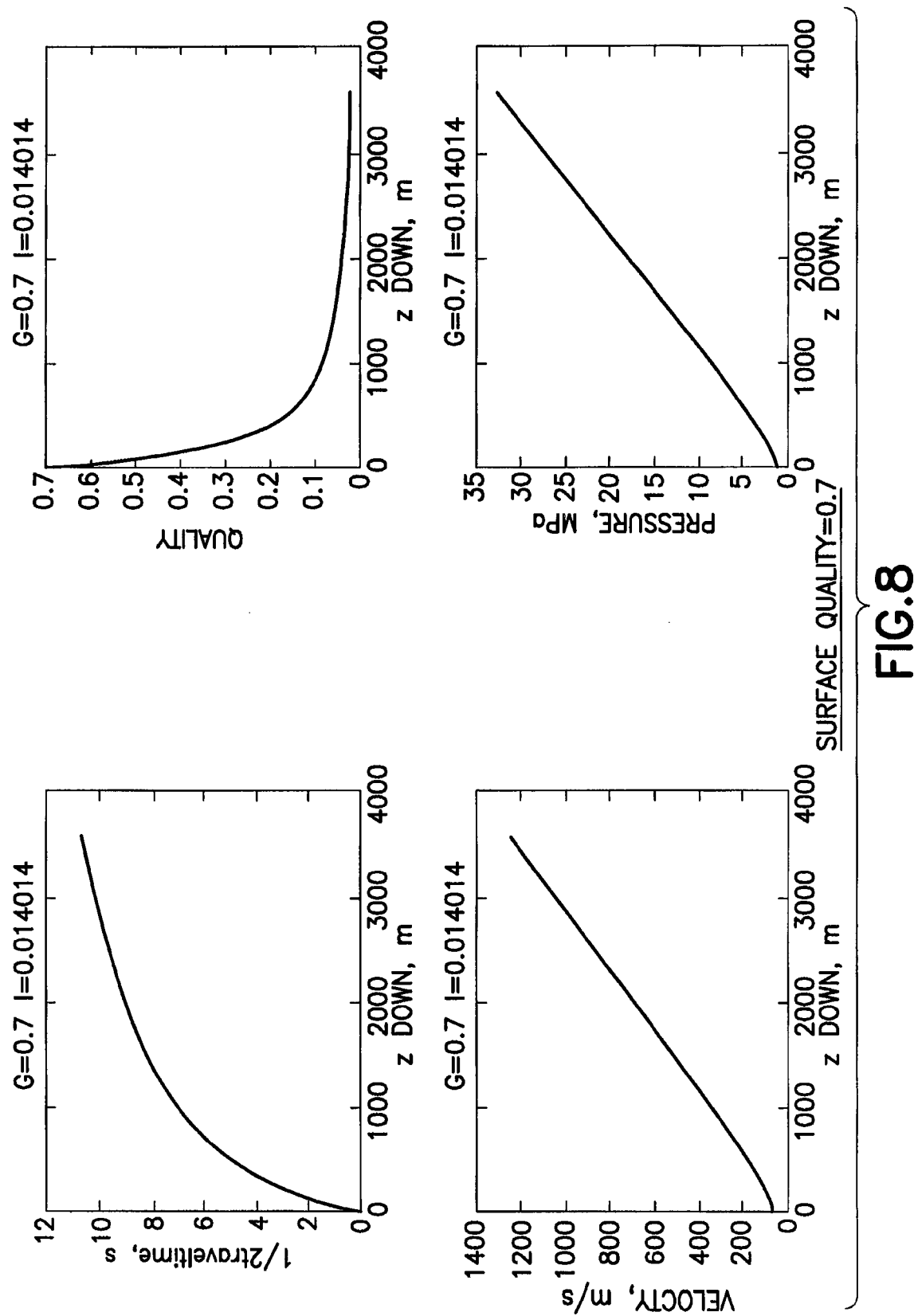
Figure 9:
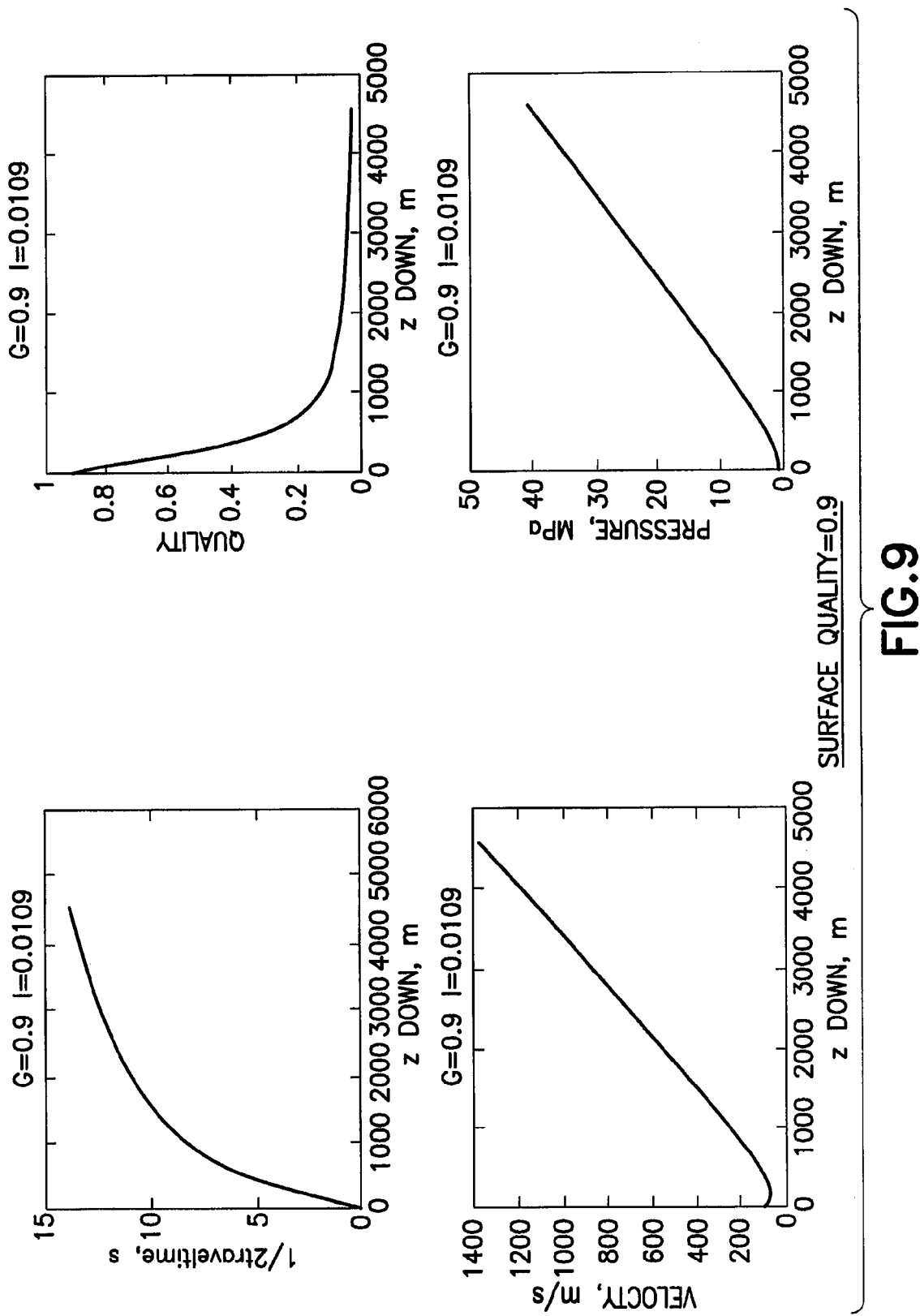
Figure 10:
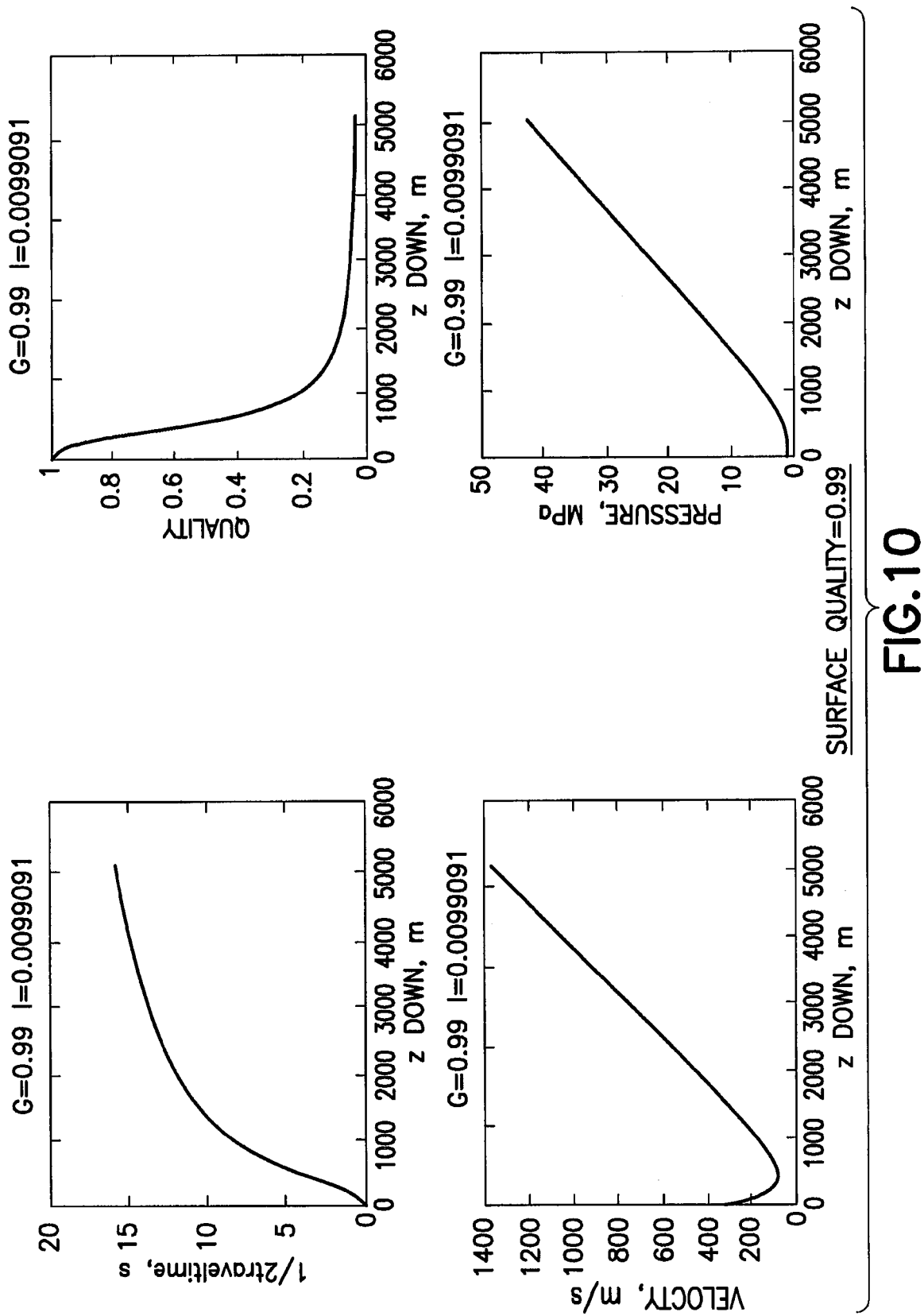

In another embodiment, at least one the above-mentioned emitter/receiver pair (1) (FIG. 3) is located in the close vicinity to the wellhead (10) of the well (4) to emit sound at the foam flow beginning (11) and to receive a signal reflected from the foam flow end (12). In another embodiment, at least one the above-mentioned emitter/receiver pair (1) could move along the flow path.

The on-line foam quality acoustic monitoring is implemented as follows. At least one emitter/receiver pair (1) (FIG. 2) is placed in the close vicinity to the foam flow. At least one acoustic pulse is emitted. Time required for the acoustic pulse to travel from the emitter (6) to the receiver (7) is recorded. Then, the acoustic pulse speed is defined (sound speed) by analyzing the acoustic response from the receiver (7). The speed of sound is defined by dividing the distance between the emitter (6) and the receiver (7) by the acoustic pulse travel time.

Pressure in the foam in the area between the emitter (6) and the receiver (7) is defined.

The foam quality $\Gamma$ is calculated as per the equation (3) in case of a foam composed of perfect gas and perfect fluid, or in more complicated cases, it can be found from the chart.

The sound speed in the foam for a special case of a two-phase medium composed of perfect gas and non-viscous perfect fluid is calculated as follows. It's worth mentioning that the speed of sound in more complex substances (e.g., multi-phase foam in the form of non-perfect gas and fluid with a complex rheology) is calculated in a similar way.

Let's consider a fluid and gas mixture at a given pressure p and temperature T. Let's denote the gas volume as $V_1$ and fluid volume as $V_2$, then the quality $\Gamma$ is defined as follows $$\Gamma = \frac{V_1}{V_1 + V_2} \quad (4)$$

The fluid state change is described by the equation $$\Delta p = -\lambda \frac{\Delta V_2}{V_2} \quad (5)$$

where:

$\lambda = \rho_{fluid} c^2$;

$\rho_{fluid}$—fluid density;

c—fluid speed.

The gas state change equation (for isothermal cases) is as follows $$\Delta p = -p \frac{\Delta V_1}{V_1} \quad (6)$$

For static case, a change in the full volume $\Delta(V_1+V_2)$, which is defined as stated below, corresponds to the change in the pressure $\Delta p$ $$\Delta(V_1 + V_2) = -\Delta p \left( \frac{V_2}{\lambda} + \frac{V_1}{p} \right) \quad (7)$$

Therefore, the analog of Lame's first parameters for the mixture is as follows $$\lambda_{mix} = -\frac{\Delta p(V_1 + V_2)}{(\Delta V_1 + \Delta V_2)} = \frac{1}{\lambda^{-1}(1-\Gamma) + \Gamma p^{-1}} \quad (8)$$

Therefore, Lame's first parameter for the mixture depends on pressure. Typically, $\lambda \sim 10^3$ MPa, at p~10 MPa, therefore, $\lambda \gg p$ and a member $\Gamma p^{-1}$ in the denominator dominates until $\Gamma < 0.01$, i.e. up to negligible gas concentrations.

This means that while calculating acoustic waves in foams, it's possible to substitute Lame's parameter in fluid to $\lambda_{mix}$ or, with a rather good accuracy, $$\lambda_{mix} \approx \frac{p}{\Gamma}, \quad (9)$$

where: p—pressure. Generally, $\lambda_{mix} \approx 10$ MPa, which is much lower than that for typical fluids.

In our calculations, fluid properties are characterized by fluid density and speed. The latter relation means that the "equivalent speed $c_{mix}$" in accordance with the below-mentioned formula can be used $$\lambda_{mix} \approx \frac{p}{\Gamma} = \rho_{mix} c_{mix}^2 \quad (10)$$

where $\rho_{mix} = \rho_{fluid}(1-\Gamma)$, wherefrom $$\frac{p}{\rho_{fluid}(1-\Gamma)\Gamma} = c_{mix}^2 \quad (11)$$

The equation (11) is not applicable for $\Gamma=0$, since the approximation is not reached. For a typical set of parameters p=10 MPa, $p_{fluid}$=1,000 kg/m$^3$, $\Gamma$=0.3, we well receive that $C_{mix}$=218 m/s.

Figure 1:
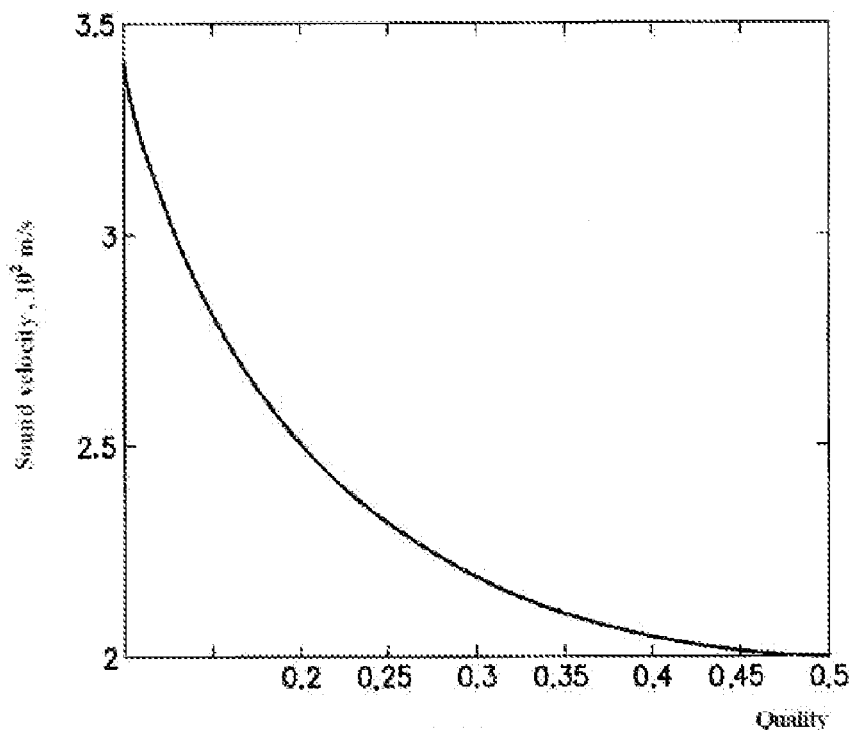
FIG. 1 shows the characteristics of sound speed in water foam at p=10 MPa.

FIG. 1 shows the sound speed $C_{mix}$ variation vs. $\Gamma$ for a case when $0 \leq \Gamma \leq 0.5$, whilst the sound speed $C_{mix}$ relation for a case when $0.5 \leq \Gamma \leq 1$ is obtained from this diagram using the formula $$c(\Gamma) = c (1-\Gamma).$$

Therefore, the calculated speed of sound in foams is significantly lower than the sound speed in fluids at pressures comparable with the fluid bulk modulus.

As follows from the $\Gamma$ vs. sound speed diagram (FIG. 1), the best case for $\Gamma$ value detection is the left part of the curve at small values of $\Gamma$. Hence, the area where $0 \leq \Gamma \leq 0.5$ or $0.85 \leq \Gamma \leq 1$ is less sensible to sound speed measurement errors (up to 10 m/s), since they do not strongly affect the $\Gamma$ value.

It's possible to theoretically calculate the foam quality distribution in wells for a simple foam discussed above, and to determine corresponding distribution of the sound speed and pressure which in practice could be measured and applied for the foam quality calculation. Calculations for other, more complex, foams were described by P. Valko et. al. in <<Rheological properties of carbon dioxide & nitrogen based foams>>.

Let's assume that L is a length of a well inclined at an angle of $\phi$ to the vertical line. Let's assume that the coordination axis z is directed along the well in a way so that the point z=0 corresponds to the wellhead and z values grow downwards. Let's consider the process when a foam fills in a well. As z values grow, the foam quality $\Gamma(z)$ reduces, which could be calculated as follows (provided that perfect gas is used for aeration).

Let's consider an infinitely thin horizontal layer in a well with the center in the point z. In this layer, gas bubbles meet the following state equation $$p(z) = \frac{ZR}{\mu}\rho_g(z)T(z) \tag{12}$$

where:

p(z)—point pressure; $\rho_g(z)$—gas density; $\mu(z)$—molecular weight of gas; T(z)—point temperature; Z—gas type dependent constant; R—universal gas constant.

Typically, gas amount in a thin layer is characterized by a function z, which is dependent on the foam injection rate. Let's assume that a quantity of gas per volume unit is independent of z, then the gas density and quality are bound by the following relation $$\rho(z)\Gamma(z)=r=\text{const}, \tag{13}$$

where r is expressed through a complete mass $M_g$ of injected gas $$r = \frac{4M_g\cos(\phi)}{\pi d^2}, \tag{14}$$

where d is pipe diameter.

Combining both two expressions, we will receive the gas state equation expressed in the foam quality terms $$p(z) = a\frac{T(z)}{\Gamma(z)}, a = \frac{ZR}{\mu}r \tag{15}$$

At the same time, p(z) is equal to a hydraulic pressure $$p(z) = p(0) + g\cos(\phi)\int_0^z \rho_{foam}(z')\,dz', \tag{16}$$

where g—free-fall acceleration.

As follows from the foam quality definition $\rho_{foam}=\rho_{fluid}(1-\Gamma)+\rho_{gas}\Gamma$.

Neglecting a small gas-related value, we'll receive that $\rho_{foam}=\rho_{fluid}(1-\Gamma)$.

Therefore, $$p(z) = p(0) + g\cos(\phi)\rho_{fluid}\int_0^z (1-\Gamma(z'))\,dz', \tag{17}$$

Form equations (15), (16), the integral equation for foam quality distribution follows:

$$a\frac{T(z)}{\Gamma(z)} = p(0) + g\cos(\phi)\rho_{fluid}\int_0^z (1-\Gamma(z'))\,dz', \tag{18}$$

Let's assume that the temperature vs. depth is a linear function that follows the below-specified empirical law $$T=T(0)+kz\cos(\phi) \tag{19}$$

Differentiating (18) by z, we'll receive the following:

$$\frac{a\Gamma(z)-\Gamma'(z)(T(0)+\alpha z)}{\Gamma^2(z)} = q(1-\Gamma(z)) \tag{20}$$

where $$q = \frac{g\cos(\phi)\rho_{fluid}}{a}, \alpha = k\cos(\phi). \tag{21}$$

Generally, $\gg q$; thus, it can be assumed in calculations that $\alpha=0$. The dependence from $\alpha$ is retained only to show the integrability of the equation at integrability at an arbitrary value $\alpha$, which can be used in case of very high temperature gradients. For an arbitrary value $\alpha$, the differential equation can be easily integrated in the algebraic form $$(T(0)+\alpha z)^\alpha = F(\Gamma(z))/F(\Gamma(0)) \tag{22}$$

$$F(\Gamma) = \left(\frac{\Gamma^2}{|\alpha-q\Gamma(1-\Gamma)|}\right)^{\frac{1}{2q}}\left(\frac{2\alpha\Gamma-q-\tilde{q}}{2\alpha\Gamma-q+\tilde{q}}\right)^{\frac{1}{2\tilde{q}}} \tag{23}$$

$$\tilde{q} = \sqrt{q^2-4q\alpha}, \tag{24}$$

which requires a numerical calculation approach. Let's assume that $\alpha=0$. Then finding the decision simplifies and is expressed as follows $$\frac{q}{T(0)}z = (F(\Gamma(z))-F(\Gamma(0))) \tag{25}$$

$$F(\Gamma) = \left(\frac{1}{\Gamma}+\ln\left|\frac{\Gamma-1}{\Gamma}\right|\right) \tag{26}$$

This means that the decision is expressed by non-dimensional depth $$\varsigma = lz, l = \frac{q}{T(0)} = \frac{g\rho_{fluid}\cos(\phi)}{p(0)\Gamma(0)} \tag{27}$$

where the scale factor l is defined by the boundary conditions at z=0.

Typical range of values for l is 0.01÷0.1.

Figure 11:
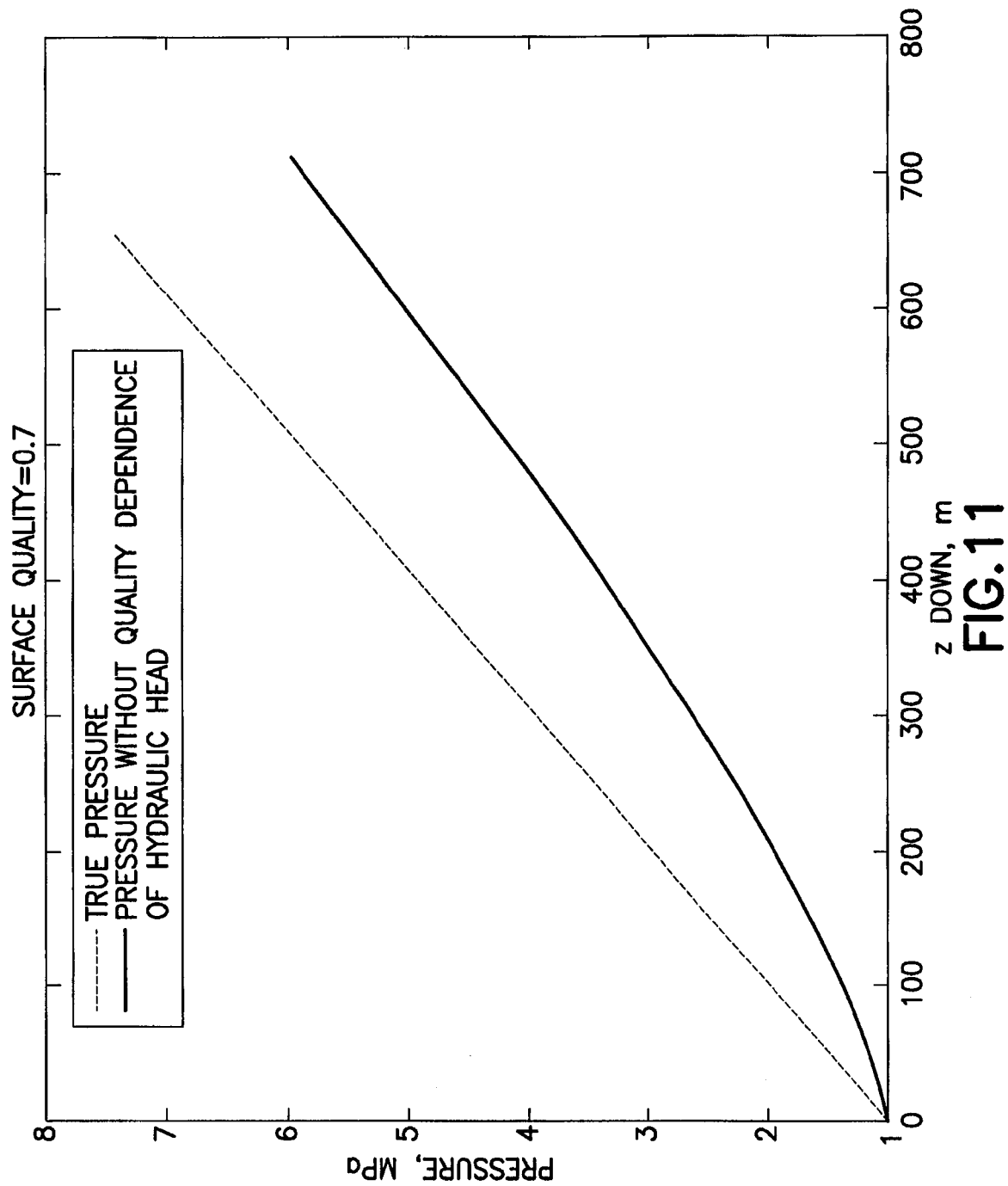
FIG. 11 shows a pressure distribution diagram for vertical wells filled with foams, as per the invention.

FIGS. 4-10 shows distribution diagrams for foam quality and associated pressure and sound speed parameters at a given pressure and fluid density at the surface, as well as the time of sound propagation from point z at various values of $\Gamma$, 1 on the surface. FIG. 11 shows a pressure distribution diagram for vertical wells filled with a foam. The upper curve is plotted on the assumption of the foam quality even distribution; the lower curve is plotted with the consideration of the wellhead pressure vs. foam quality relationship. As for the sound speed measurement in foams, attention should be paid to the following. The above-mentioned sound speed measurement process delivers satisfactory results for unconfined media. However, it requires some modification to be applied for a case of wave propagation in confined media, in particular, in pipes which is typical for both a formation fracturing process and well cementing process. This is explained by the fact that any local emitter generates both pure P-waves in the foam and other wave types, e.g., P- and S-waves in the rock and their images (head P- and S-waves) in the tube, as well as a tube wave whose speed is slightly lower than the speed of the P-wave in the foam. Since tube waves are featured with a dispersion property, the initial pulse disperses as far as it propagates. That's why it's necessary to specially process signal to isolate the P-wave from the recorded signal. This processing could be made as described below.

Since the sound speed in foams $C_{foam}$ is many-fold less than the speed of P- and S-waves in rocks and the speed of the tube wave is also (but slightly) less than the sound speed in foams, the arrival of the P-wave and tube wave significantly lags behind the arrival of the head P- and S-waves. This delay is much bigger than in case of non-confined media. Thus, recorded signals of the head P- and S-waves can be neglected and only remaining waves should be taken into consideration; of the remaining waves, the most rapid component corresponds to the foam's P-wave. Therefore, the speed of sound in foams $C_{foam}$ could be defined by recording the first arrival of the wave which comes much later than the head P- and S-waves.

On the other side, since the sound speed vs. foam quality curve (FIG. 1) shows that very steep sections for small and large values of the foam quality $\Gamma$ occur, it was found out that significant errors in $C_{foam}$ do not strongly influence $\Gamma$. That's why the determination of the foam quality becomes more reliable for small and large values of $\Gamma$.

An option, when at least one emitter/receiver pair (1) is moved along the foam flow path and the sound speed is measured at several points en-route the foam flow direction, is possible. The indicated data are applied for getting the foam quality distribution along the flow path.

It's also possible to install an emitter/receiver pair at the wellhead to emit sound at the foam flow beginning and to receive the signal reflected from the foam flow end. The foam quality distribution is calculated using a preset formula linking a complete time for signal propagation from the emitter to the receiver with sound peed distribution in the foam. The example of this kind of analysis in shown above.

For monitoring of continuous distribution of the foam quality, pressure along the foam flow path is continuously measured using, e.g., optic fiber, which allows foam quality measurement to expedite, since there is no need to move the emitter-receiver pair en-route the flow. Once the foam quality distribution along the flow path or along a certain flow line section is determined, the results can be compared with the preset values, which are required to perform certain kind of the above-mentioned services. Based on the results obtained, a decision to proceed without modifications and to change the foam composition is taken. This procedure can be repeated several times or implemented continuously as far as work proceeds.

INDUSTRIAL APPLICABILITY

The suggested device and method allows the on-line foam quality monitoring, in particular, in hard-to-reach areas, during well cementing or formation fracturing operations.

What is claimed is:

1. A method for on-line foam quality acoustic monitoring comprising the steps of:
   placing at least one emitter/receiver pair in close vicinity to a foam flow,
   emitting at least one acoustic pulse,
   recording travel time within which the acoustic pulse travels from the emitter to the receiver,
   determining acoustic pulse speed or sound speed by analyzing an acoustic response of the receiver, measuring pressure in the foam in the area between the emitter and receiver, and calculating foam quality $\Gamma$ using an equation:

$$\Gamma = \frac{1}{2} \pm \sqrt{\frac{1}{4} - \frac{N}{\rho_{fl}} \frac{p}{C_{fm}^2}},$$

where $C_{fm}$—speed of sound in the foam, p—pressure, $\rho_{fl}$—fluid density, $\Gamma$—foam quality, N—polytrophic expansion coefficient, wherein the reference value, N=1 for isothermal process; and N=1.4 for adiabatic process.

2. The method of claim 1 further comprising the steps of moving at least one emitter/receiver pair along a foam flow path and measuring sound speed at several points en-route the foam flow path to obtain a foam quality distribution along the foam flow path.

3. The method of claim 2 further comprising the step of measuring pressure along at least one extended section en-route the foam flow path to monitor uninterrupted the foam quality distribution.

4. A device for on-line foam quality acoustic monitoring comprising:
   at least one emitter/receiver pair located in close vicinity of a foam flow and intended to emit at least one acoustic pulse and to receive at least one acoustic response,
   a logger to record a time required for the acoustic pulse to travel from the emitter to the receiver,
   a pressure transducer placed between the emitter and receiver, and
   a data processing unit connected to at least one emitter/receiver, the logger and pressure transducer, which calculates a sound speed using the acoustic pulse travel time, and to calculate the foam quality $\Gamma$ based on data received from an equation:

$$\Gamma = \frac{1}{2} \pm \sqrt{\frac{1}{4} - \frac{N}{\rho_{fl}} \frac{p}{C_{fm}^2}},$$

Where $C_{fm}$—speed of sound in the foam, p—pressure, $\rho_{fl}$—fluid density, $\Gamma$—foam quality, N—polytrophic expansion coefficient, wherein the reference value, N=1 for isothermal process; and N=1.4 for adiabatic process.

5. The device of claim 4, for use in well cementing or formation fracturing wherein the at least one emitter/receiver pair is located at a wellhead or in a close vicinity to the wellhead to emit sound at the foam flow beginning and to receive a signal reflected from the foam flow end.

6. The method of claim 1 for use in well cementing or formation fracturing.

7. The method of claim 1 wherein if the foam is composed of a perfect gas and a perfect fluid and the foam quality is less than ½ or greater than ½, the sign to be selected in the said formula is <<−>> and <<+>> respectively.

8. The method of claim 1 wherein the foam quality - pressure and sound speed in the foam chart is deduced analytically, experimentally or through a numerical simulation.

9. The method of claim 6 wherein at least one emitter/receiver pair is located at a wellhead or in a close vicinity to the wellhead to emit sound at the foam flow beginning and to receive a signal reflected from the foam flow end.

10. A method of claim 6 further comprising the step of comparing the calculated foam quality value with the foam quality required for cementing or fracturing operations and maintaining a quality value within a preset range.

* * * * *